(12) United States Patent
Murray et al.

(10) Patent No.: US 9,861,781 B2
(45) Date of Patent: Jan. 9, 2018

(54) INTERMITTENT CATHETER ASSEMBLY

(71) Applicant: Hollister Incorporated, Libertyville, IL (US)

(72) Inventors: Michael G. Murray, Ballina (IE); James McIlvenna, Dublin (IE); Martin P. Creaven, Ballina (IE); Adam J. Foley, Ballina (IE); David Hannon, Ballina (IE); Daniel O'Brien, Calry (IE); Padraig M. O'Flynn, Castlegar (IE)

(73) Assignee: Hollister Incorporated, Libertyville, IL (US)

( * ) Notice: Subject to any disclaimer, the term of this patent is extended or adjusted under 35 U.S.C. 154(b) by 517 days.

(21) Appl. No.: 14/395,359

(22) PCT Filed: Mar. 14, 2013

(86) PCT No.: PCT/US2013/031221
§ 371 (c)(1),
(2) Date: Oct. 17, 2014

(87) PCT Pub. No.: WO2013/158270
PCT Pub. Date: Oct. 24, 2013

(65) Prior Publication Data
US 2015/0133898 A1    May 14, 2015

Related U.S. Application Data

(60) Provisional application No. 61/636,218, filed on Apr. 20, 2012.

(51) Int. Cl.
*A61M 25/00* (2006.01)
*A61F 5/44* (2006.01)
*A61F 5/442* (2006.01)

(52) U.S. Cl.
CPC .......... *A61M 25/002* (2013.01); *A61F 5/44* (2013.01); *A61F 5/442* (2013.01); *A61F 5/4404* (2013.01);
(Continued)

(58) Field of Classification Search
CPC .......... A61M 25/002; A61M 25/0045; A61M 25/0017; A61M 2025/0046;
(Continued)

(56) References Cited

U.S. PATENT DOCUMENTS 2,784,716 A * 3/1957 Broman .............. A61M 3/0262
128/DIG. 24
2,856,932 A * 10/1958 Griffitts .............. A61M 25/002
128/DIG. 24

(Continued)

FOREIGN PATENT DOCUMENTS

| DE | 202005009947 U1 | 9/2005 |
| EP | 2686054 B1 | 12/2014 |
| WO | WO 03008029 A2 | 1/2003 |

OTHER PUBLICATIONS

Notification of Transmittal of the International Search Report, International Search Report and Written Opinion for PCT/US2013/031221 dated Jul. 9, 2013.
(Continued)

*Primary Examiner* — Adam Marcetich
(74) *Attorney, Agent, or Firm* — Cook Alex Ltd.

(57) ABSTRACT

An intermittent catheter assembly is disclosed which comprises an intermittent catheter having a proximal insertion end, a distal end remote from the proximal insertion end, and an insertable portion. The insertable portion of the catheter extends from the proximal insertion end thereof to a point approaching the distal end thereof. The catheter is disposed in a cavity and a drawstring secured to the catheter extends
(Continued)

through the cavity and generally along the insertable portion of the catheter. The drawstring has a first end secured to the catheter between the insertable portion and the distal end and a second end outside the cavity for withdrawing the catheter therefrom. The drawstring exits the cavity proximate the proximal insertion end of the catheter to accommodate drawing the proximal insertion end thereof from the cavity into the urethral opening by pulling on the second end of the drawstring.

16 Claims, 12 Drawing Sheets

(52) U.S. Cl.
CPC ....... *A61F 5/4407* (2013.01); *A61M 25/0017* (2013.01); *A61M 25/0045* (2013.01); *A61M 2025/0046* (2013.01); *A61M 2202/0496* (2013.01)

(58) Field of Classification Search
CPC ....... A61M 2202/0496; A61M 25/0111; A61F 5/4404; A61F 5/44; A61F 5/442; A61F 5/4407; Y10S 128/24; B65D 25/102; B65D 27/38; B65D 55/06; B65D 63/10; B65D 75/66; B65D 75/68; B65D 77/32; B65D 2555/025; B65D 2571/00641
See application file for complete search history.

(56) References Cited

U.S. PATENT DOCUMENTS

| | | | | |
|---|---|---|---|---|
| 3,478,743 A * | 11/1969 | Ericson | ............... | A61F 5/4404 285/12 |
| 3,762,399 A * | 10/1973 | Riedell | ............... | A61M 25/002 600/580 |
| 3,991,758 A * | 11/1976 | Mohrke | ............ | B65D 75/5822 604/403 |
| 4,379,506 A * | 4/1983 | Davidson | ............ | A61M 25/002 206/364 |
| 5,226,530 A * | 7/1993 | Golden | ............... | A61M 25/002 206/210 |
| 5,865,819 A * | 2/1999 | Cisko, Jr. | ................ | A61F 5/445 604/327 |
| 6,004,305 A * | 12/1999 | Hursman | .................. | A61F 5/44 600/544 |
| 6,578,709 B1 | 6/2003 | Kavanagh et al. | | |
| 8,523,843 B2 | 9/2013 | Kavanagh et al. | | |
| 2004/0133226 A1* | 7/2004 | Buckman | ............ | A61B 17/3415 606/167 |
| 2004/0163980 A1* | 8/2004 | Tanghoj | .................... | A61F 5/44 206/363 |
| 2005/0234390 A1* | 10/2005 | Buckman | ............ | A61B 17/3415 604/22 |
| 2005/0240163 A1* | 10/2005 | Andersen | ............... | A61F 5/4404 604/332 |
| 2007/0289887 A1* | 12/2007 | Murray | ............... | A61M 25/002 206/364 |
| 2009/0131917 A1 | 5/2009 | Kavanagh et al. | | |

OTHER PUBLICATIONS

Japanese Office Action, dated Dec. 1, 2015, for Japanese Patent Application No. 2015-507001.
Canadian Office Action dated Nov. 9, 2015, for Application No. 2,870,936, entitled: Intermittent Catheter Assembly.

\* cited by examiner

INTERMITTENT CATHETER ASSEMBLY

RELATED APPLICATION

This is a U.S. National Stage of PCT International Patent Application No. PCT/US2013/031221, Mar. 14, 2013, which claims the benefit of and priority to U.S. Provisional Patent Application No. 61/636,218, filed Apr. 20, 2012, both of which are hereby incorporated by reference.

FIELD OF THE DISCLOSURE

The present disclosure is generally directed to an intermittent catheter assembly for insertion by a user through the urethra for draining urine from the human bladder and, more particularly, to an intermittent catheter assembly capable of being utilized for sterile intermittent catheterization by users who may be suffering from reduced or limited hand dexterity.

BACKGROUND OF THE DISCLOSURE

Intermittent catheter assemblies are a good option for many users who suffer from various abnormalities of the urinary system. A common situation is where single use packaged, sterile ready-to-use catheters are utilized. An important criterion for single use ready-to-use products is that they be entirely user-friendly under a wide variety of different conditions.

Among those requiring intermittent catheterization on a regular and recurring basis are users who suffer from reduced or limited hand dexterity. There has been a continuing need for an intermittent catheter assembly for users on the verge of self-intermittent catheterization, but who have been unable to avail themselves of this technique to enjoy the freedom it would provide due to the absence of suitable catheter products. In this connection, there is a significant and growing segment of catheter users who have reduced or limited gripping ability and limb functionality.

To consider the needs of such catheter users, it is useful to understand cervical vertebrae breaks and the affected nerves of spinal cord injuries. For those users having injuries ranging from the C6 to the C8 vertebrae, research has shown that such injuries may result in reduced or limited arm, hand, wrist and/or finger movements. However, there are also other catheter users who have a wide range of dexterity issues which have resulted from many different health issues.

Regardless of the reason, a person having reduced or limited arm, hand, wrist and/or finger dexterity who requires regular and recurring catheterization may not be able to perform self-intermittent catheterization but could potentially do so if there was available an intermittent catheter assembly that could be used without the need for significant manual dexterity.

To provide an intermittent catheter assembly suitable for users of limited manual dexterity, it is important to consider various aspects of self-catheterization. These include providing a discrete assembly that will facilitate ease of i) inserting the catheter without compromising sterility, ii) draining urine from the bladder, and iii) discarding the intermittent catheter assembly. If these aspects of self-catheterization could be addressed, a person having reduced or limited manual dexterity would be better able to perform this procedure.

SUMMARY OF THE DISCLOSURE

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

An intermittent catheter assembly is disclosed which comprises an intermittent catheter having a proximal insertion end, a distal end remote from the proximal insertion end, and an insertable portion. The insertable portion of the intermittent catheter extends from the proximal insertion end to a point approaching the distal end. The intermittent catheter is disposed in a guide sleeve or channel and a drawstring secured to the intermittent catheter extends through the guide sleeve or channel along the insertable portion of the catheter. The drawstring has a first end secured to the intermittent catheter between the insertable portion and the distal end and a second end located outside the guide sleeve or channel. The drawstring exits the guide sleeve or channel proximate the proximal insertion end of the intermittent catheter to accommodate drawing the proximal insertion end from the guide sleeve or channel. The drawstring also facilitates drawing the proximal insertion end and at least part of the insertable portion of the intermittent catheter into the urethra until the proximal insertion end is in the bladder.

In an exemplary embodiment, the intermittent catheter assembly comprises a package defining a cavity, and an opening is provided in the package. An intermittent catheter is disposed within the cavity in such manner that the proximal insertion end of the catheter is located at or near an opening in the package. Also, a drawstring secured to the intermittent catheter extends from the package at or near the opening for withdrawing the catheter through the opening.

The drawstring permits the proximal insertion end of the intermittent catheter to be drawn through the opening in the package into the urethral opening and also permits at least part of the insertable portion of the intermittent catheter to be drawn through the opening in the package and into the urethra until the proximal insertion end is suitably located in the bladder.

In another exemplary embodiment, the packaged intermittent catheter assembly comprises a tray formed to have a channel. An intermittent catheter is disposed in the channel such that the proximal insertion end of the catheter is located at or near an opening in the tray. Additionally, a drawstring secured to the intermittent catheter extends from the tray at or near the opening for withdrawing the catheter from the channel.

The drawstring permits the proximal insertion end of the intermittent catheter to be drawn through the opening in the tray into the urethral opening and also permits at least part of the insertable portion of the intermittent catheter to be drawn through the opening in the tray and into the urethra until the proximal insertion end is in the bladder.

In other respects, the channel formed in the tray can be generally U-shaped and can extend from the opening in the tray to a point remote therefrom so that the intermittent catheter can be guided by the U-shaped channel during withdrawal through the opening in the tray. Further, a lubricating mechanism can be located within the tray for lubricating at least the proximal insertion end of the intermittent catheter prior to or during withdrawal of the intermittent catheter through the opening in the tray. Additionally, the lubricating mechanism can be either a gel lubricant, or it can comprise a hydrophilic surface on at least a portion of the intermittent catheter and a hydrating agent within the tray for hydrating or activating the hydrophilic surface. Still further, the hydrating agent within the tray may comprise a vapor releasing strip which is disposed within the channel formed in the tray and a gas permeable material can be provided for the purpose of separating the intermittent catheter from contact with the vapor releasing strip.

In still other respects, the drawstring can include a first end secured to the intermittent catheter and a second end outside the tray, and a finger loop can be associated with the second end for withdrawing the catheter. The tray can also include an introducer tip which is located externally of the tray and generally adjacent an end of the channel which defines the opening through which the intermittent catheter can be withdrawn. In addition, the tray can comprise a vacuum formed lid and base and the introducer tip can normally be sealed by a removable foil cover having the drawstring attached and having a finger loop and tear slit formed therein.

Other features can include a urine drainage opening through the tray at a location remote from the opening through which the intermittent catheter is withdrawn and a removable seal can normally cover the urine drainage opening. Then, the drawstring can be secured to the removable seal as well as to the catheter to thereby cause the urine drainage opening to open during withdrawal of the intermittent catheter from the tray as a result of pulling on the drawstring.

In yet another exemplary embodiment, the packaged intermittent catheter assembly comprises a urine collection bag formed to have a channel or sleeve. An intermittent catheter is disposed in the channel or sleeve such that the proximal insertion end is located at or near an opening in the urine collection bag. Further, a drawstring secured to the intermittent catheter extends from the bag at or near the opening in the bag for withdrawing the catheter.

The drawstring permits the proximal insertion end of the intermittent catheter to be drawn through the opening in the bag into the urethral opening and also permits at least part of the insertable portion of the intermittent catheter to be drawn through the opening in the bag and into the urethra until the proximal insertion end is in the bladder.

In other respects, the channel or sleeve can be generally straight and extend from the opening in the bag to a point remote therefrom so the intermittent catheter can be guided by the channel or sleeve during withdrawal from the bag. The bag can be generally rectangular in shape and the channel or sleeve can comprise a generally straight, shape-retaining tube adjacent and generally parallel to one of a pair of long edges of the bag, and the bag can include a gripping handle formed as a sealed void in the bag. The gripping handle can extend adjacent and generally parallel to the tube and also adjacent one of a pair of short edges of the bag, and the bag can include a drainage port adjacent the other of the pair of long edges opposite the tube.

In still other respects, the drainage port can include a peelable seal for opening the drainage port to drain the bag while gripping the tube through the gripping handle, and the peelable seal can have a finger hole accessible through a cut-out defined by the sealed void forming the gripping handle for removing the seal while gripping the tube through the gripping handle to drain the bag.

In a variation on the foregoing, the channel or sleeve can be generally U-shaped and can extend from the opening in the bag to a point remote therefrom. Again, the bag can be generally rectangular in shape and the channel or sleeve can be formed of a U-shaped tube having leg portions adjacent and generally parallel to each of a pair of opposed long edges of the bag which can include a gripping handle. In this variation of the packaged intermittent catheter assembly, the gripping handle can be disposed between the leg portions of the U-shaped tube closer to one of the leg portions of the tube than the other and adjacent one of a pair of short edges of the bag.

In addition to the foregoing, a lubricating mechanism can be located within the package or within the urine collection bag for lubricating the intermittent catheter. The lubricating mechanism can comprise a gel lubricant for contact with at least the proximal insertion end of the intermittent catheter prior to or during withdrawal of the proximal insertion end of the intermittent catheter from the packaging or the urine collection bag. Alternatively, the lubricating mechanism may comprise a hydrophilic surface on at least the proximal insertion end and the insertable portion of the intermittent catheter and a hydrating agent in the package or in the urine collection bag for hydrating or activating the hydrophilic surface.

An introducer tip can be located externally of the bag adjacent an end of the channel or sleeve to define the opening through which the proximal insertion end and the insertable portion of the intermittent catheter are withdrawn. A removable cap can cover the introducer tip, and the drawstring can include a first end secured to the catheter and a second end passing through the introducer tip and attached to the cap. Further, a finger loop can be formed in the removable cap and the drawstring can be attached to the removable cap and also provided with a slack portion outside of the urine collection bag prior to withdrawal of the intermittent catheter.

Still other advantages and features of the present disclosure will be apparent from the detailed description which follows when taken in conjunction with the accompanying drawings.

DETAILED DESCRIPTION OF THE DISCLOSURE

Figure 1:
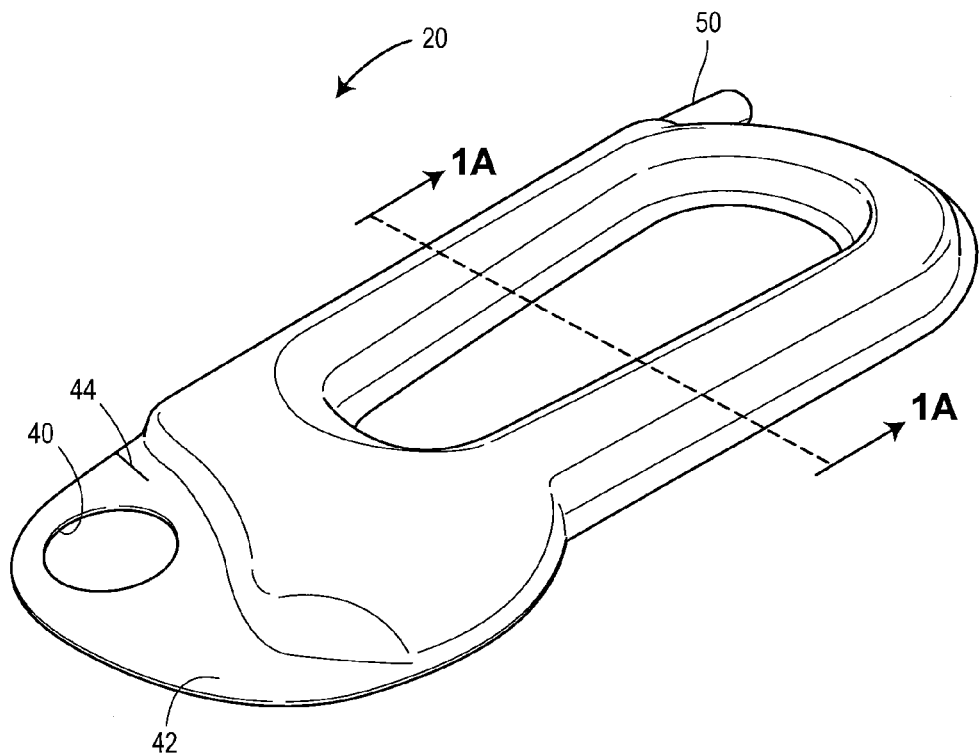
FIG. 1 is a perspective view of a packaged intermittent catheter assembly in accordance with a first exemplary embodiment of the disclosure.
Figure 1A:
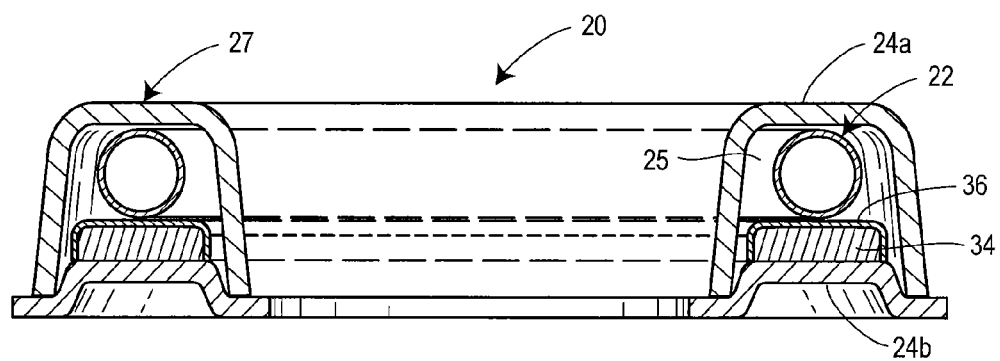
FIG. 1A is a cross-sectional view taken along the line 1a-1a of FIG. 1 and illustrating an intermittent catheter within the packaged assembly of FIG. 1.
Figure 2:
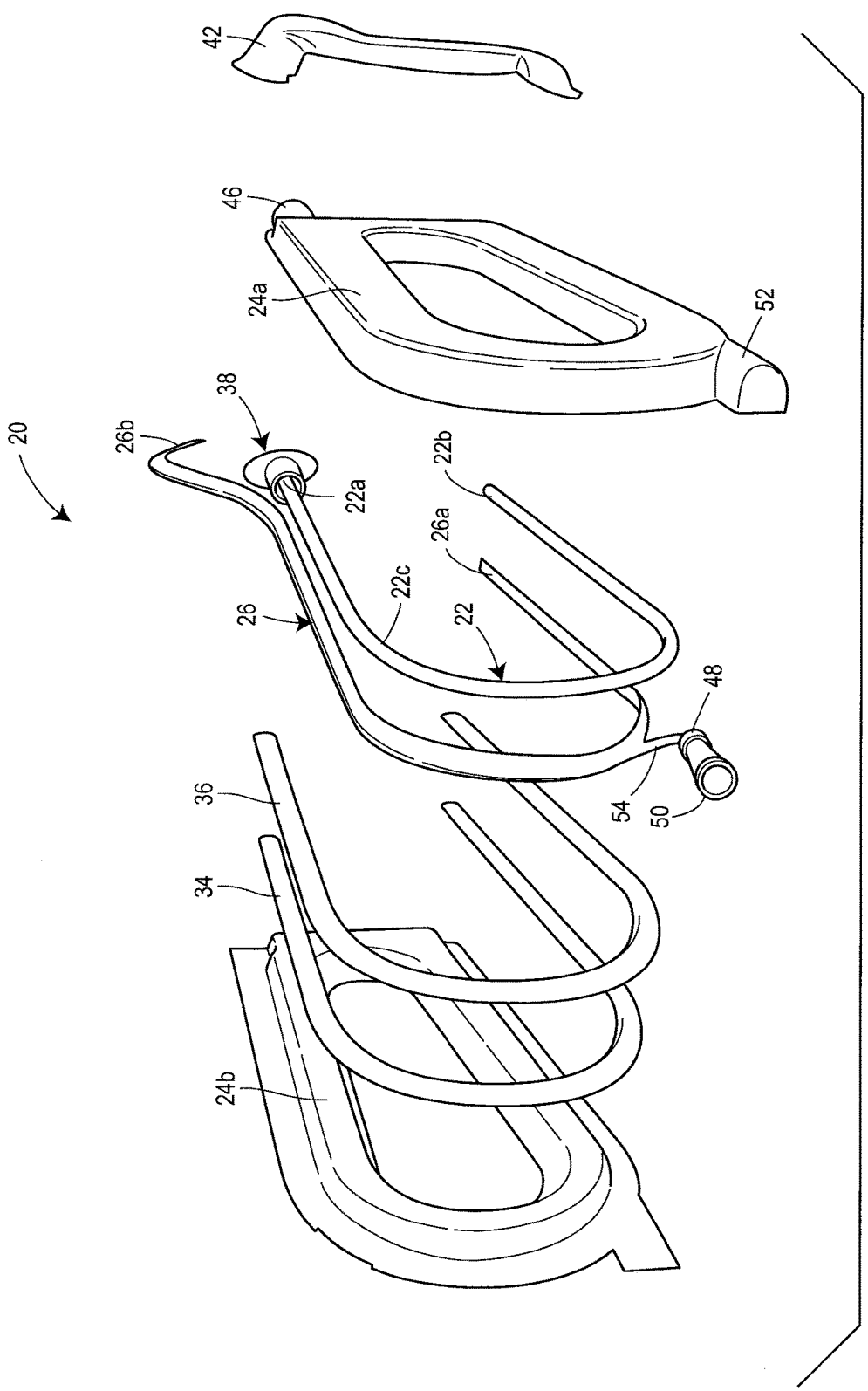
FIG. 2 is an exploded perspective view illustrating all of the various components of the exemplary embodiment of the packaged assembly of FIG. 1.
Figure 3:
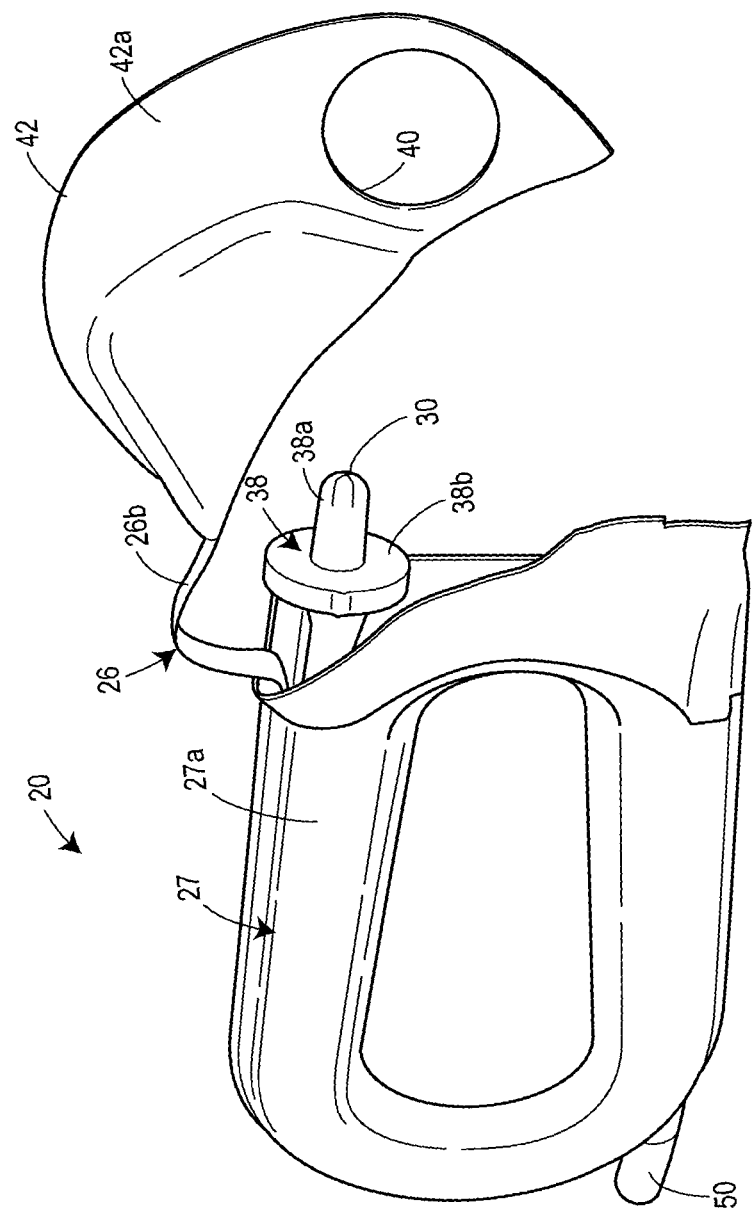
FIG. 3 is a perspective view depicting a first step for using the intermittent catheter contained within the packaged assembly illustrated in FIG. 1.
Figure 4:
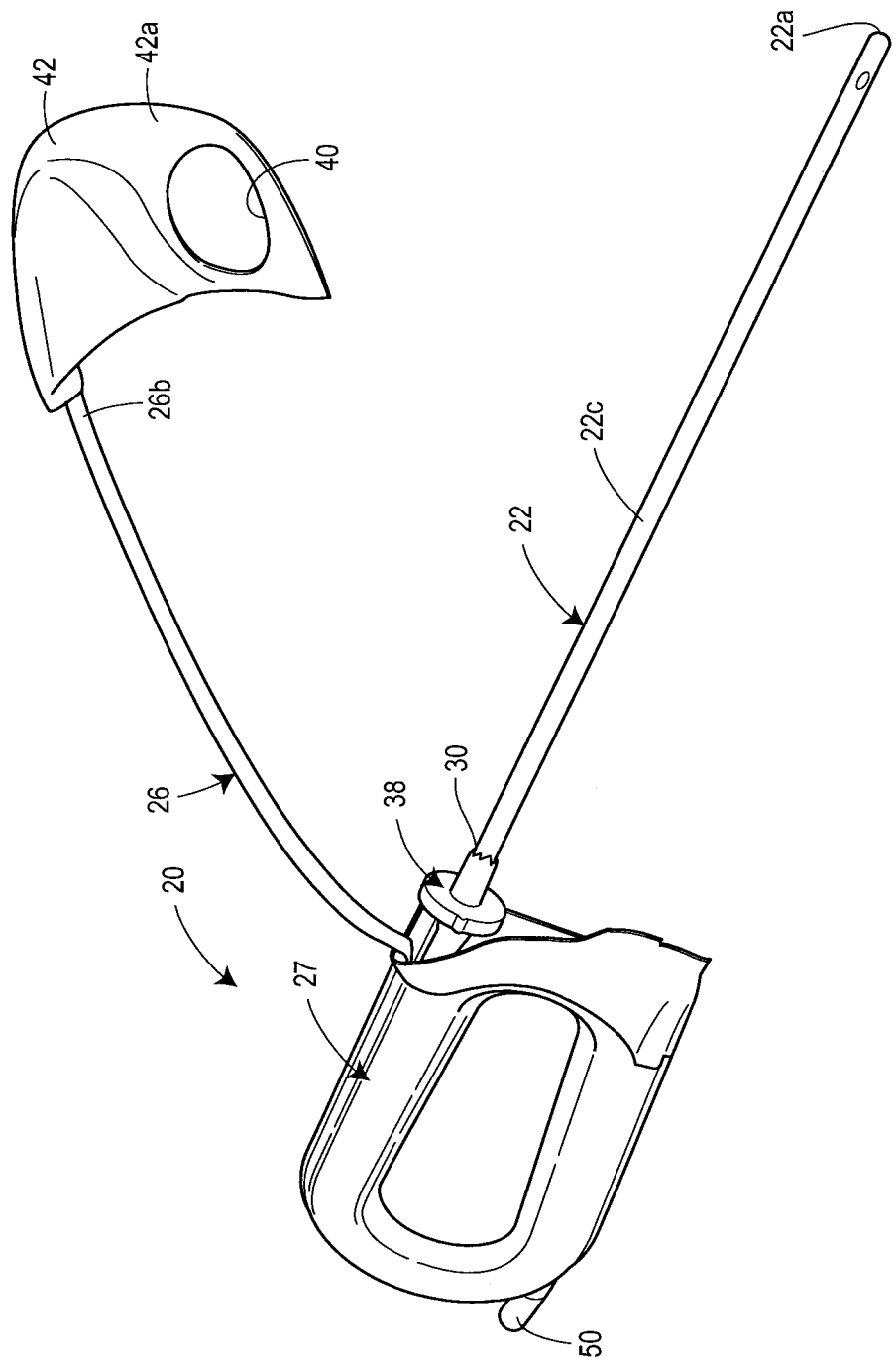
FIG. 4 is a perspective view depicting a second step for using the intermittent catheter contained within the packaged assembly illustrated in FIG. 1.
Figure 5:
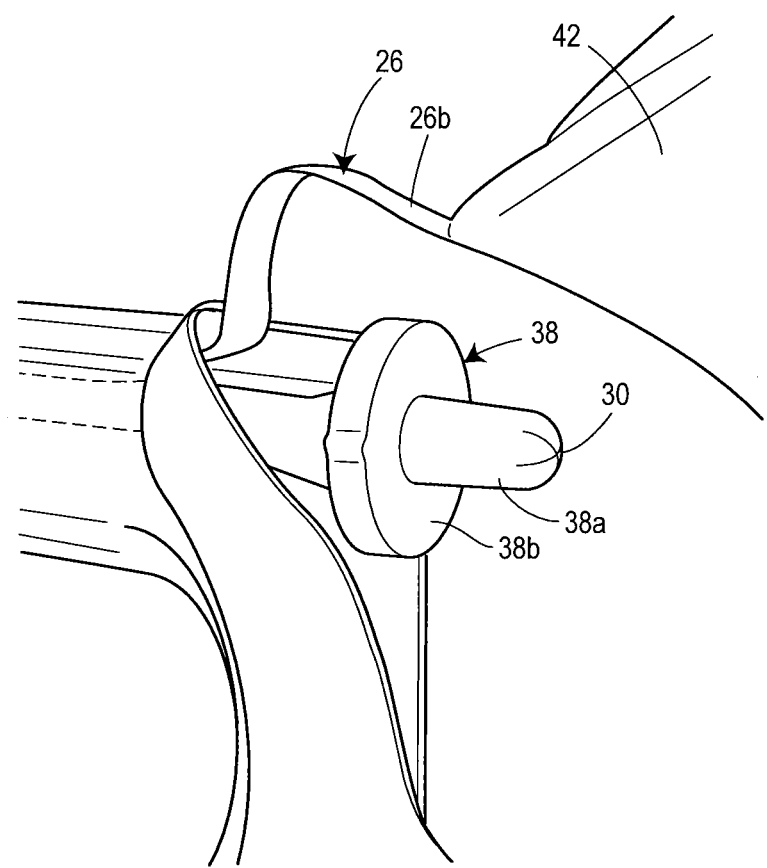
FIG. 5 is a close-up perspective view of a portion of the packaged assembly of FIG. 3 illustrating an introducer tip, drawstring and gripping handle.
Figure 6:
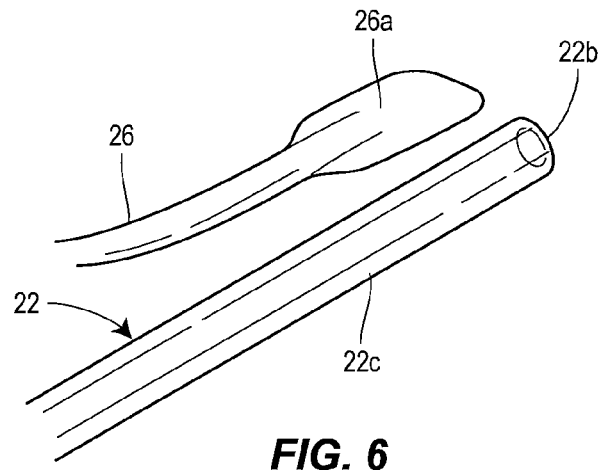
FIG. 6 is a perspective view illustrating the distal end of an intermittent catheter and a drawstring prior to attaching the drawstring to the catheter.
Figure 7:
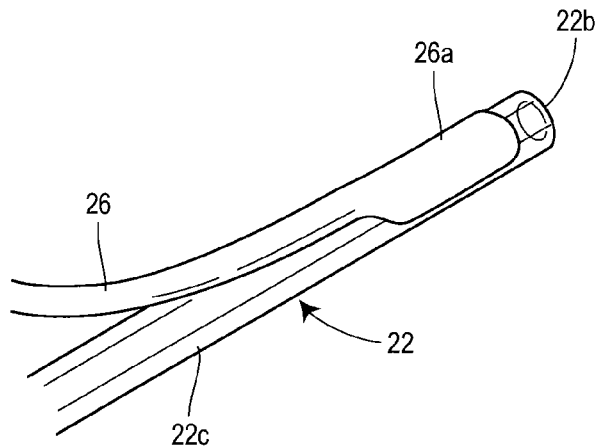
FIG. 7 is a perspective view illustrating the distal end of an intermittent catheter and a drawstring after the drawstring is attached to the catheter.

In the illustrations given, and with reference first to FIGS. 1-4, the reference numeral 20 designates generally an intermittent catheter assembly which comprises an intermittent catheter 22 contained in a package which can be formed of package components 24a, 24b (see, in particular, FIGS. 1a and 2). As best shown in FIGS. 2 and 4, the intermittent catheter 22 will be seen to have a proximal insertion end 22a, a distal end 22b remote from the proximal insertion end 22a, and an insertable portion 22c. The insertable portion 22c of the intermittent catheter 22 will be understood to extend generally from the proximal insertion end 22a to a point which at least approaches the distal end 22b thereof. The intermittent catheter 22 is disposed in a channel 25 defined by the package components 24a, 24b, and a drawstring 26 secured to the intermittent catheter 22 extends substantially through the channel 25. In particular, the drawstring 26 extends from at or near the distal end 22b of the intermittent catheter 22 along the insertable portion 22c to a point near the proximal insertion end 22a. Referring to FIGS. 5-7, the drawstring 26 has a first end 26a secured to the intermittent catheter 22 between the insertable portion 22c and the distal end 22b and a second end 26b outside of the channel 25 for withdrawing the intermittent catheter 22 from within the channel 25 defined by the package components 24a, 24b.

Referring to FIGS. 3 and 4, the drawstring 26 exits the channel 25 proximate the proximal insertion end 22a of the intermittent catheter 22 to accommodate drawing the proximal insertion end 22a from the channel 25 into the urethral opening by pulling on the second end 26b of the drawstring 26. The drawstring 26 also permits at least part of the insertable portion 22c of the intermittent catheter 22 to be drawn from the channel 25 through the urethral opening into the urethra until the proximal insertion end 22a is in the bladder. In the foregoing, it will be understood that the proximal insertion end 22a of the intermittent catheter 22 will have typical drainage openings and comprises that part of the insertable portion 22c of the intermittent catheter 22 that first enters the urethral opening during an intermittent catheterization procedure.

As discussed, the intermittent catheter assembly 20 comprises the package components 24a, 24b forming the channel or cavity 25. FIG. 2 illustrates that the intermittent catheter 22 will be disposed within the channel or cavity 25 so that the proximal insertion end 22a of the catheter 22 is located at or near an opening 30 (also see FIG. 3). FIG. 3 illustrates that the drawstring 26 secured to the intermittent catheter 22 extends from the assembly 20 at or near the opening 30.

The assembly 20 can comprise a package or tray 27 formed by the package components 24a, 24b to have a curved guide sleeve, channel or cavity 25. The intermittent catheter 22 is disposed in the curved guide sleeve, channel or cavity 25 such that the proximal insertion end 22a is located at or near the opening 30 in the package or tray 27 formed by the package components 24a, 24b. The drawstring 26 secured to the intermittent catheter 22 extends from the package or tray 27 at or near the opening 30 as best shown in FIGS. 3 and 4.

The drawstring 26 permits the proximal insertion end 22a of the intermittent catheter 22 to be drawn through the opening 30 in the package or tray 27 and into the urethral opening and also permits at least part of the insertable portion 22c of the intermittent catheter 22 to be drawn through the opening 30 in the package or tray 27 and into the urethra until the proximal insertion end 22a having drainage openings is in the bladder for draining urine through the catheter 22.

Referring to FIGS. 1, 1a and 3, the curved guide sleeve, channel or cavity 25 formed in the package or tray 27 can be generally U-shaped and extend from the opening 30 in the package or tray 27 to a point opposite and remote therefrom so the intermittent catheter 22 can be guided during withdrawal through the opening 30. A lubricating mechanism can be located within the package or tray 27 for lubricating at least the proximal insertion end 22a of the intermittent catheter 22 either prior to or during withdrawal of the intermittent catheter 22 from the package or tray 27. The lubricating mechanism can comprise either a gel lubricant, or a hydrophilic surface on at least a portion of the intermittent catheter 22 and a hydrating agent within the package or tray 27 for hydrating or activating the hydrophilic surface portion of the intermittent catheter 22 to facilitate catheter insertion. Further, the hydrating agent disposed within the package or tray 27 may comprise a vapor releasing strip 34 disposed within the guide sleeve, channel or cavity 25 formed in the package or tray 27 and a gas permeable material 36 can separating the intermittent catheter 22 so it cannot come into contact with the vapor releasing strip 34 (see FIGS. 1a and 2).

Where the lubricating mechanism is a hydrophilic surface on at least a portion of the intermittent catheter 22, the hydrating agent disposed within the package or tray 27 could also take the form of a burstable pouch of water, or the package or tray 27 could be provided with an opening to be exposed a short time before using the intermittent catheter 22 for adding water to the guide sleeve, channel or cavity 25 to hydrate the hydrophilic surface portion of the catheter.

If the lubricating mechanism comprises a gel lubricant, the gel can be placed in the guide sleeve, channel or cavity 25 of the package or tray 27 for contact with the intermittent catheter 22 or, alternatively, the gel can be located in an introducer tip 38 so it will be applied to the intermittent catheter 22 as it is being drawn through the opening 30 formed in the end thereof.

Referring to FIGS. 3, 6 and 7, the drawstring 26 having a first end 26a secured to the intermittent catheter 22 and a second end 26b outside of the package or tray 27 can have a finger loop 40 associated with the second end 26b for withdrawing the intermittent catheter 22 from the package or tray 27. The package or tray 27 can also include the introducer tip 38 externally of the package or tray 27 and adjacent an end of the guide sleeve, channel or cavity 25 to define the opening 30 through which the intermittent catheter 22 is withdrawn. As will be appreciated from FIG. 2, the package or tray 27 can comprise a vacuum formed lid 24a and base 24b and the introducer tip 38 can be sealed by a removable shrink wrap foil cover 42 to which the drawstring 26 is attached and which has the finger loop 40 and a tear slit 44 formed therein.

As will be understood from FIG. 2, the vacuum formed lid 24a can be formed to have a cylindrical tubular extension 46 to which the introducer tip 38 can be attached and through which the opening 30 in the introducer tip 38 will be in communication with the guide sleeve, channel or cavity 25 for withdrawing the intermittent catheter 22.

Figure 8:
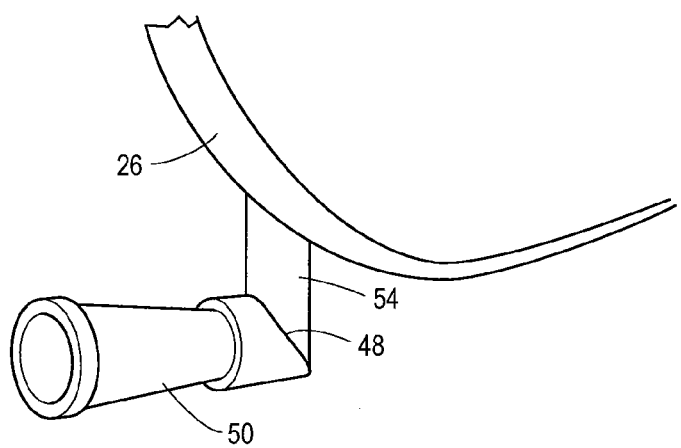
FIG. 8 is a close-up perspective view showing a drawstring attached to a seal covering a urine drainage opening in the packaged assembly of FIG. 1.

Further features can include a urine drainage opening 48 through the package or tray 27 along the guide sleeve, channel or cavity 25 remote from the opening 30 through which the intermittent catheter 22 is withdrawn. The urine drainage opening 48 can be in a conventional funnel 50 attached within a cylindrical tubular extension 52 formed in the vacuum formed lid 24a (see FIG. 2) and a seal 54 can be provided to normally cover the urine drainage opening 48 but be removed for draining urine from the package or tray 27. The drawstring 26 can be secured to the removable seal 54 as will be appreciated from FIG. 8 so that it will open the urine drainage opening 48 during withdrawal of the intermittent catheter 22 from the package or tray 27.

With regard to the foregoing, it should be noted that the package or tray 27 can be vacuum formed and sized to have sufficient rigidity and dimensional constraint to permit the guide sleeve, channel or cavity 25 to guide the intermittent catheter 22 through the guide sleeve, channel or cavity 25 under the pulling force of the drawstring 26 at or near the distal end 22b in a manner which will prevent the intermittent catheter 22 from being able to buckle on itself.

While in the foregoing, the element 26 has been denoted a "drawstring", it will be appreciated that this term is intended to cover a string, filament, tape or any other similar elongated structure capable of being strong enough to perform the intended function while also being flexible, lightweight and small enough to extend through a guide sleeve, channel, cavity or tube to exert a pulling force on a distal end of a catheter from a location proximate a proximal end of the catheter sufficient to perform self-intermittent catheterization.

Referring to FIGS. 9-14, the packaged intermittent catheter assembly comprises a urine collection bag 150 having a channel or sleeve 152. An intermittent catheter 154 is disposed in the channel or sleeve 152 in the urine collection bag 150 such that the proximal insertion end 154a is located at or near an opening 156 in the bag 150. Further, a drawstring 158 secured to the intermittent catheter 154 extends from the urine collection bag 150 at or near the opening 156.

Figure 9:
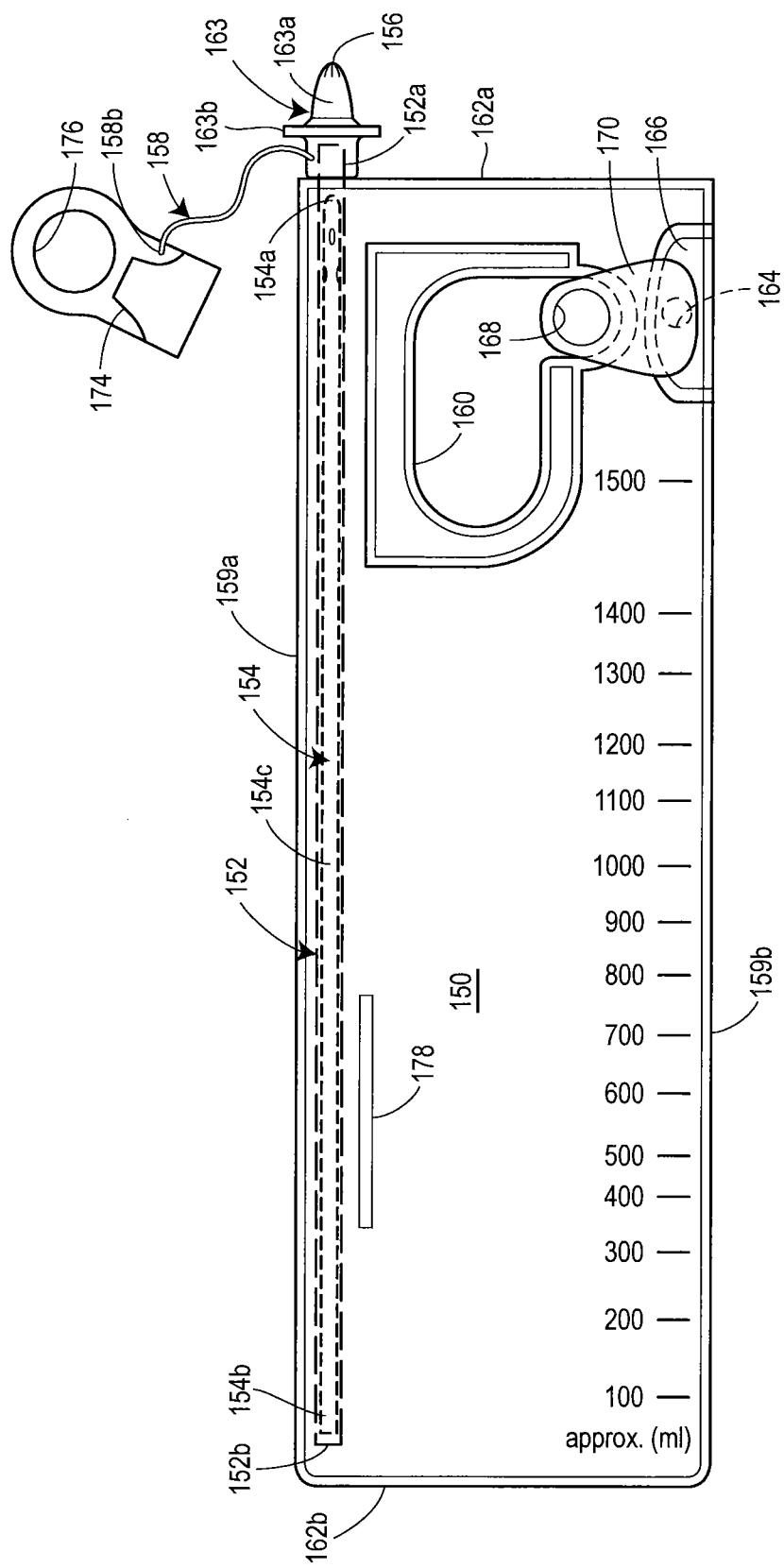
FIG. 9 is a top plan view of a packaged intermittent catheter assembly in accordance with a second exemplary embodiment of the disclosure.
Figure 10:
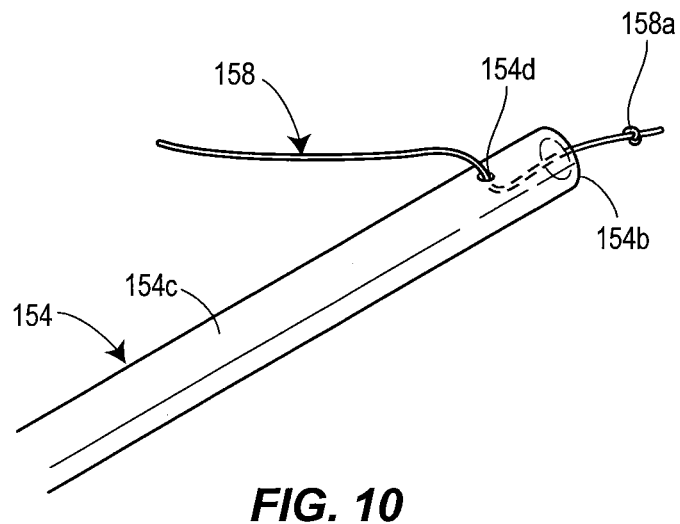
FIG. 10 is a perspective view illustrating the distal end of an intermittent catheter and of a drawstring as it is being attached to the catheter.
Figure 11:
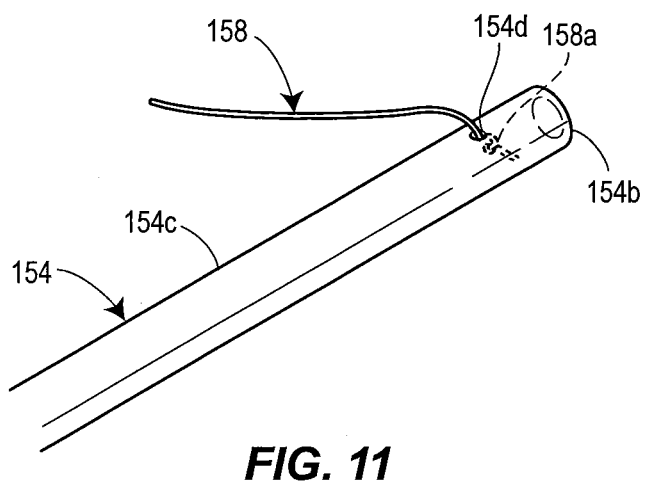
FIG. 11 is a perspective view illustrating the distal end of an intermittent catheter and of a drawstring following attachment to the catheter.

Referring to FIGS. 10 and 11, the drawstring 158 has a first end 158a secured to the intermittent catheter 154 between the insertable portion 154c and a distal end 154b and a second end 158b (FIG. 9) outside of the channel or sleeve 152 for withdrawing the intermittent catheter 154 from within the channel or sleeve 152. As shown, the drawstring 158 may comprise a filament which can be threaded through a small opening as at 154d near the distal end 154b of the intermittent catheter 154 and which can be knotted as at 158a. By forming the knot as at 158a, the drawstring 158 can exert a pulling force on the distal end 154b of the intermittent catheter 154 when the thumb or other finger has been placed through a finger loop 176 and a pulling force is applied to a removable cap 174 to which the second end 158b of the drawstring is attached.

The drawstring 158 permits the proximal insertion end 154a of the intermittent catheter 154 to be drawn through the opening 156 in the bag 150 into the urethral opening and also permits at least part of the insertable portion 154c of the intermittent catheter 154 to be drawn through the opening 156 in the bag 150 and into the urethra until the proximal insertion end 154a is disposed within the bladder for draining urine through the intermittent catheter 154.

As shown in FIG. 9, the channel or sleeve 152 can be generally straight and extend from the opening 156 in the bag 150 to a point remote therefrom so that the intermittent catheter 154 can be guided by the channel or sleeve 152 during withdrawal from the bag 150, which can be generally rectangular. The channel or sleeve 152 can comprise a generally straight, shape-retaining tube having sufficient rigidity to avoid buckling, and it can be located adjacent and extend generally parallel to one edge 159a of a pair of long edges 159a, 159b of the generally rectangular urine collection bag 150 illustrated in FIG. 9. The bag 150 can include a gripping handle 160 defined by a sealed void and formed by heat sealing the edges of the two sheets of film forming the bag 150 around the void such that the gripping handle 160 can extend adjacent and generally parallel to the tube 152. Still referring to FIG. 9, the gripping handle 160 can extend adjacent one edge 162a of a pair of short edges 162a, 162b of the generally rectangular bag 150, and the bag 150 can include a drainage port 164 located generally adjacent the long edge 159b, opposite the tube 152 and the gripping handle 160, and adjacent the short edge 162a.

Figure 12:
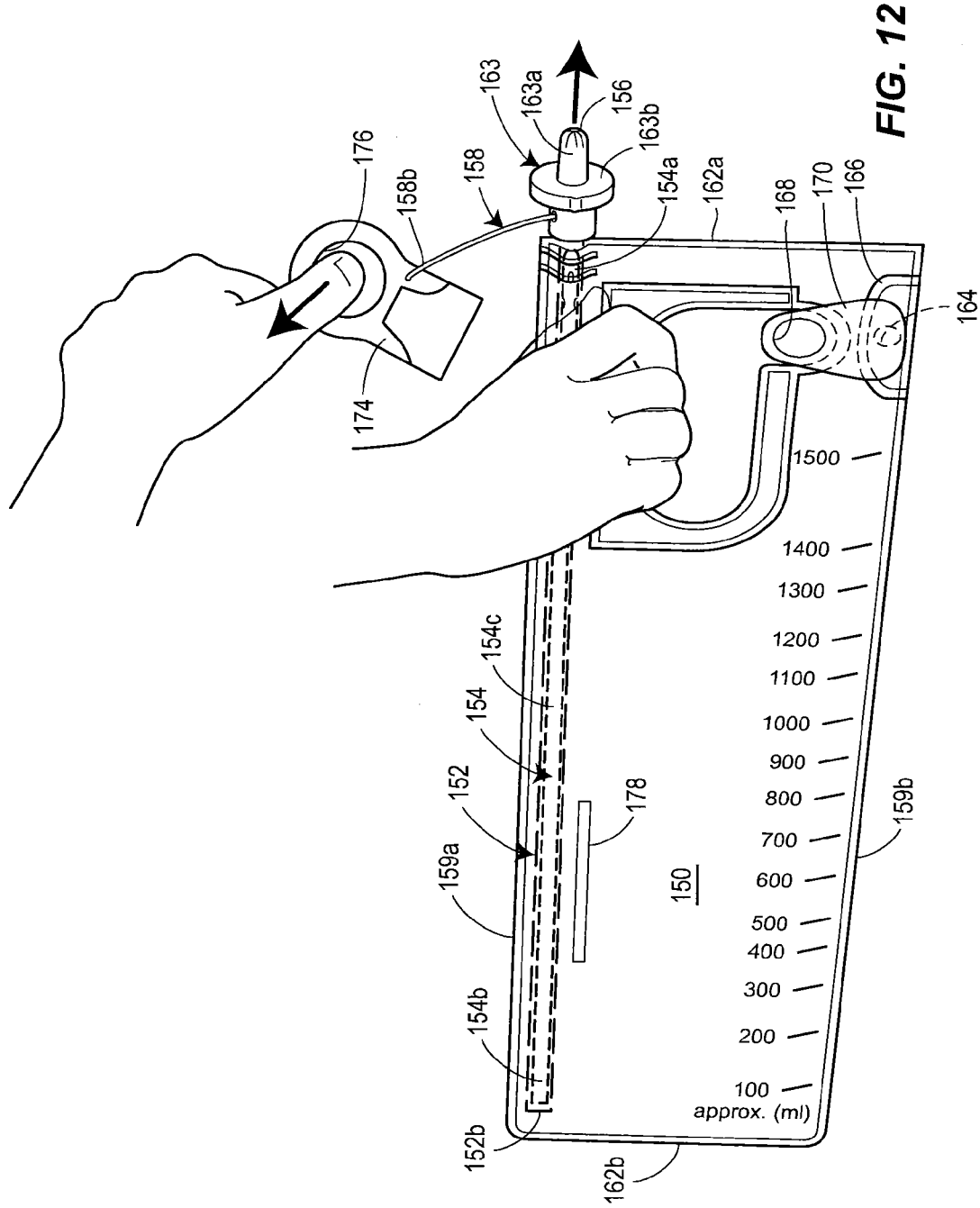
FIG. 12 is a perspective view illustrating the manner of using the intermittent catheter contained in the packaged assembly of FIG. 9.
Figure 13:
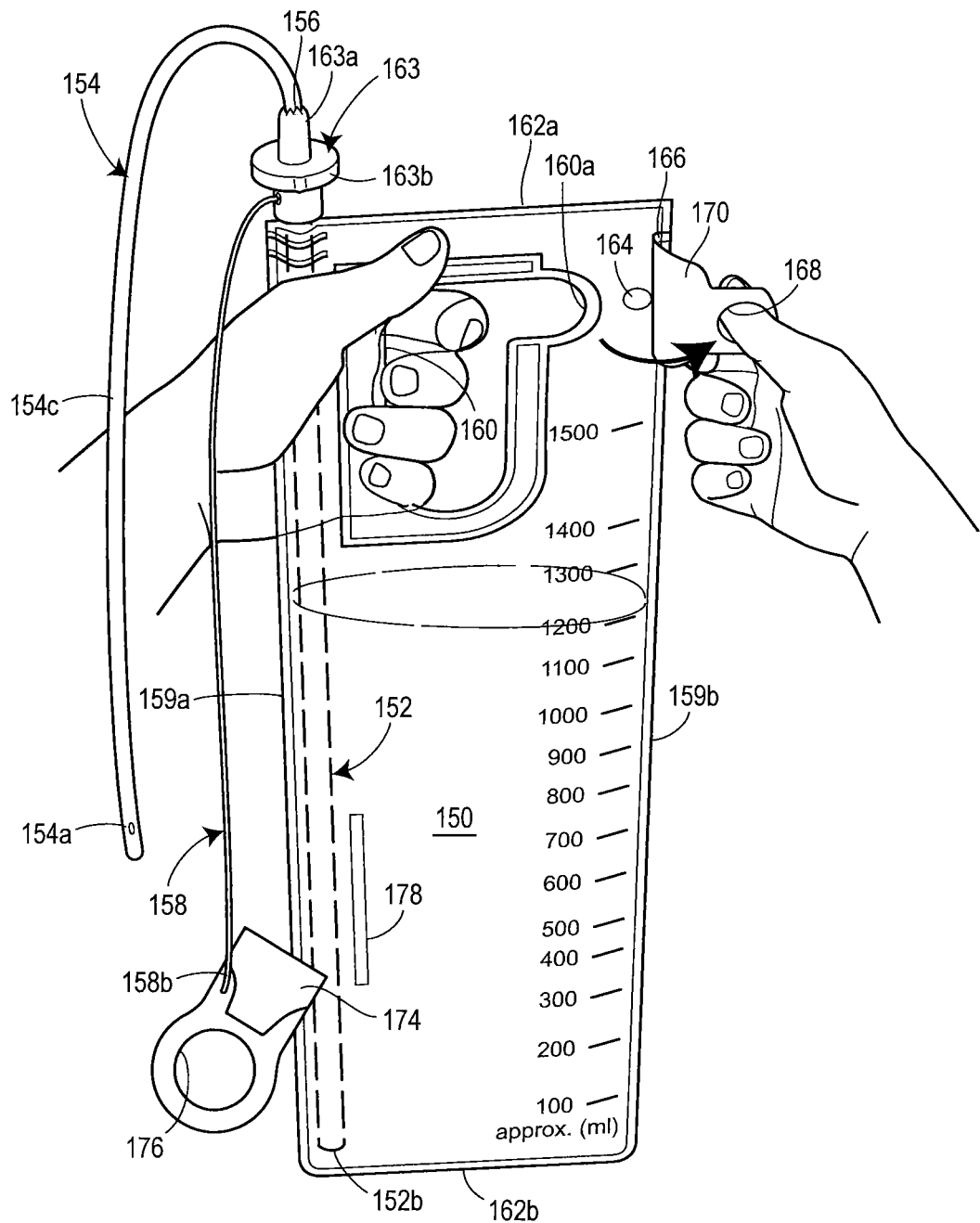
FIG. 13 is a perspective view illustrating a first step for draining the packaged assembly after using the intermittent catheter of FIG. 9.

Referring to FIGS. 9, 12 and 13, the drainage port 164 can include a peelable seal 166 for opening the drainage port 164 to drain the bag 150 while gripping the tube 152 through the gripping handle 160. The peelable seal 166 can have a finger hole 168 through an extension 170 of the peelable seal 168 which is accessible through a cut-out 160a. The cut-out 160a (FIG. 13) is also defined by the sealed void forming the gripping handle 160, and it facilitates removing the seal while still gripping the tube 152 through the gripping handle 160 to drain the bag 150. In a variation on the foregoing, the channel 152' in FIG. 9a can be generally U-shaped and can extend from the opening 156 in the bag 150 to a point remote therefrom. Again, the bag 150 can be generally rectangular in shape and, in this variation, the channel 152' can be formed of a U-shaped tube 152' having leg portions 152a' and 152b' adjacent and generally parallel to each of the pair of opposed long edges 159a and 159b of the bag 150, and the bag 150 can again include a gripping handle 160. In this variation, the gripping handle 160 can be disposed between the leg portions 152a' and 152b' of the U-shaped tube 152' and, preferably, closer to one of the leg portions 152a' than the other leg portion 152b' to facilitate gripping the leg portion 152a'.

Figure 9A:
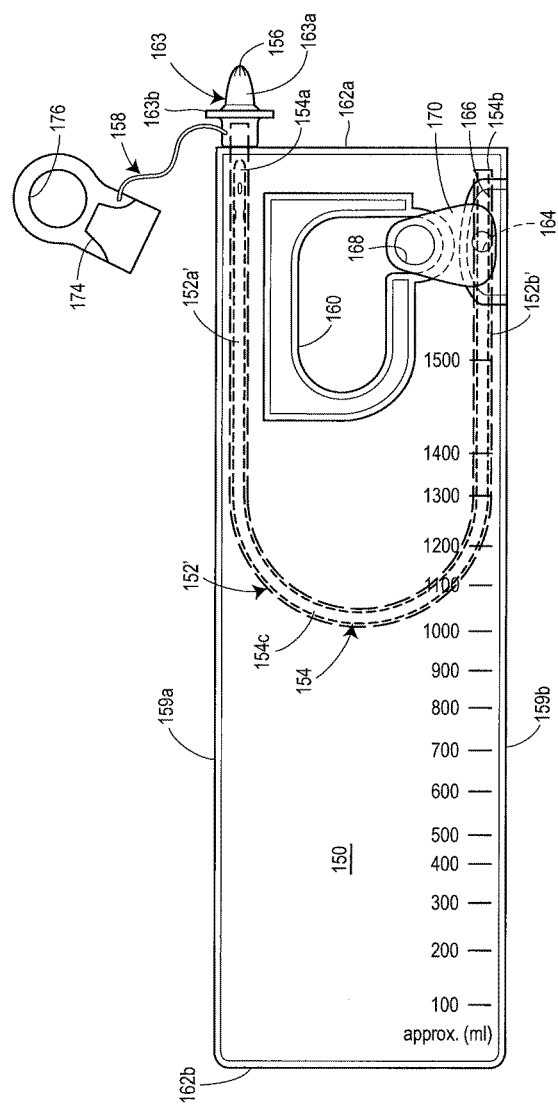
FIG. 9A is a top plan view of the packaged intermittent catheter assembly similar to FIG. 7 but illustrating a slightly modified version thereof.

In addition to the foregoing, a lubricating mechanism can be located within the urine collection bag 150 for lubricating the intermittent catheter 154 in either of the embodiments illustrated in FIGS. 9 and 9a. The lubricating mechanism can comprise a gel lubricant provided within the tubes 152, 152' or, alternatively, within an introducer tip 163, for contact with at least the proximal insertion end 154a of the intermittent catheter 154 and, preferably, also the insertable portion 154c, prior to or during withdrawal of the proximal insertion end 154a of the intermittent catheter 154 through the opening 156 in the bag 150. Alternatively, the lubricating mechanism may comprise a hydrophilic surface on at least the proximal insertion end 154a and the insertable portion 154c of the intermittent catheter 154 and a hydrating agent in the urine collection bag for hydrating or activating the hydrophilic surface of the intermittent catheter 154.

The hydrating agent within the bag 150 may comprise a vapor releasing strip (such as 34 in FIGS. 1a and 2) disposed to be substantially co-extensive with the intermittent catheter 154. Further, a gas permeable material (such as 36 in FIGS. 1a and 2) can cover the vapor releasing strip in the bag 150 to isolate it from urine collected from use of the intermittent catheter 154. Thus, the tubes 152 and 152' can be formed of a gas permeable material to permit vapor released by the vapor releasing strip to hydrate the hydrophilic surface of the intermittent catheter 154.

Where the lubricating mechanism is a hydrophilic surface on at least a portion of the intermittent catheter 154, the hydrating agent disposed within the bag 150 could also take the form of a burstable pouch of water in which case the tubes 152 and 152' will either be formed of a liquid permeable material or will be sized large enough to permit loose water in the bag 150 to reach and hydrate the hydrophilic surface a short time before using the intermittent catheter 154.

In either of the embodiments of FIGS. 9 and 9a, the introducer tip 163 can be located externally of the bag 150 on or adjacent an end (such as 152a of the tube 152) to define the opening 156 through which the proximal insertion end 154a and the insertable portion 154c of the intermittent catheter 154 is withdrawn. The removable cap 174 can cover the introducer tip 163 in either embodiment, and the drawstring 158 can include a first end 158a secured to the intermittent catheter 154 and a second end 158b passing through the introducer tip 163 and attached to the cap 174 in either embodiment. Further, a finger loop 176 can be formed in the removable cap 174 in either embodiment, and the drawstring 158 can be attached to the removable cap 174 and also provided with a slack portion in either embodiment (see FIGS. 9 and 9a) outside of the urine collection bag 150 prior to withdrawing the intermittent catheter.

Figure 14:
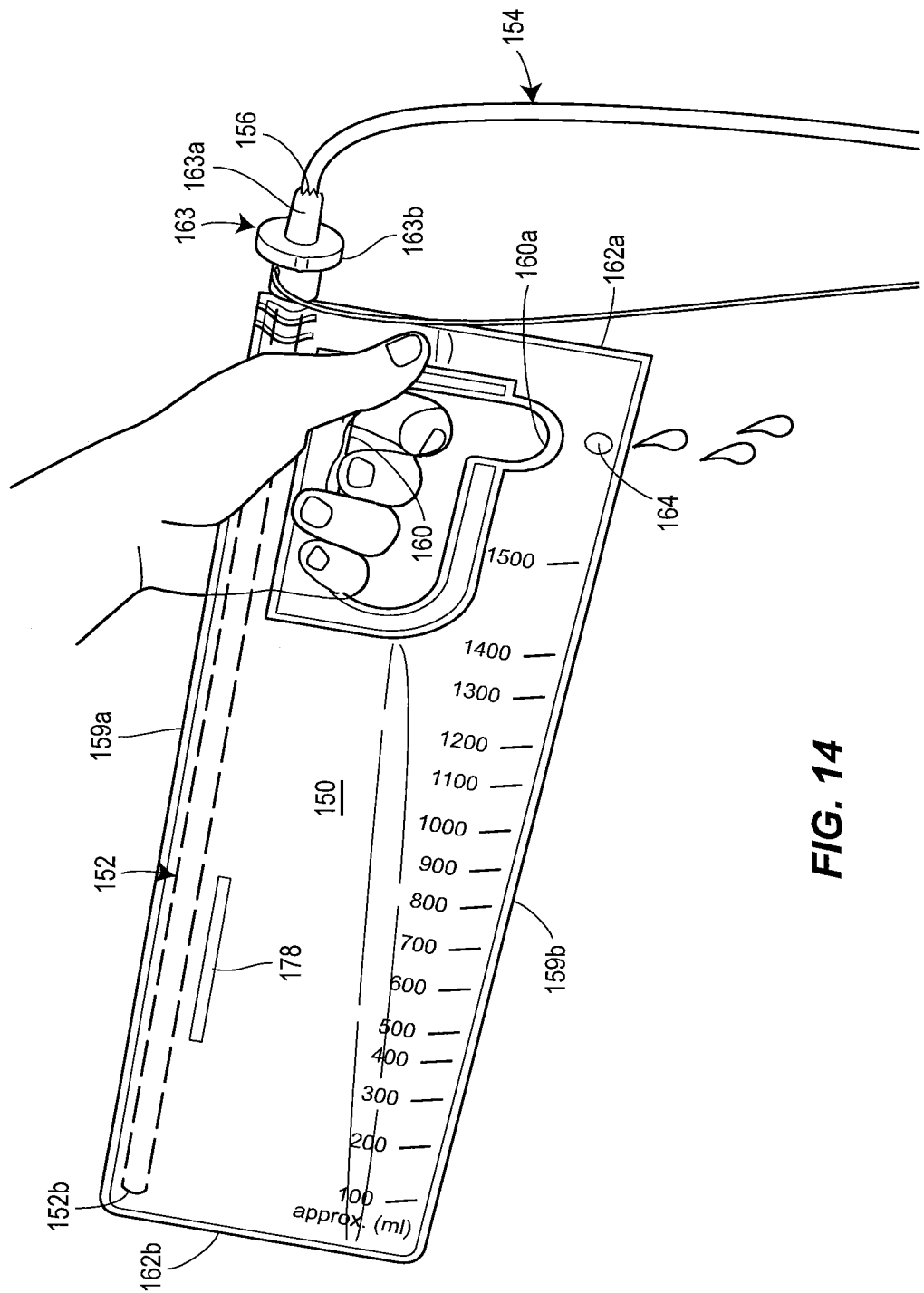
FIG. 14 is a perspective view illustrating a second step for draining the packaged assembly after performing the first step of FIG. 13.

Referring to FIGS. 12-14, the use of the urine collection bag 150 and intermittent catheter 154 for self-catheterizing can be understood. First, the user can place one hand through the gripping handle to grip around the shape-retaining tube as shown in FIG. 12. Next, the user can place a finger or thumb through the finger loop 176 and remove the cap 174 as also shown in FIG. 12. When this has been done, the user can insert the conical end 163a of the introducer tip 163 into the urethral opening until the flange 163b abuts the urethral opening. Next, the user can use the thumb placed through the finger loop 176 to pull on the drawstring 158. This will cause the proximal insertion end 154a of the intermittent catheter 154 to be drawn through the opening 156 into the urethral opening. Further pulling on the drawstring 158 will cause the proximal insertion end 154a to be drawn through the urethra and into the bladder. The user will stop pulling on the drawstring 158 when urine starts to flow. This will be visually evident as urine from the bladder passes through the intermittent catheter into the bag 150. At this point the proximal insertion end 154a will be properly located in the bladder and at least part of the insertable portion 154c will be located within the urethra while the distal end will still be within the tube 152.

As shown, the tube 152 is maintained in position adjacent and generally parallel to the long edge 159a of the bag 150 by a heat seal as at 178. The end of the tube 152 will be seen to extend from a point adjacent or near the opening as at 152a to a point as at 152b near but spaced from the short edge 162b of the bag 150. This facilitates urine exiting the intermittent catheter 154 within the tube 152 and passing through the tube 152 into the urine collection bag 150.

After urine has been drained from the bladder, the intermittent catheter 154 can be removed from the urethra by withdrawing the introducer tip 163 from the urethral opening and continuing to move the bag 150 away from the urethral opening. The bag 150 can then be supported as shown in FIG. 13 using the gripping handle 160. The thumb or other finger of the free hand not holding the bag 150 can then be inserted through the finger hole 168 to remove the peelable seal 166 to thereby open the drainage port 64 for draining urine from the bag 150.

Referring to FIG. 14, the urine collection bag 150 can continue to be gripped through the gripping handle and tilted as shown to drain urine in the bag 150 through the drainage port 164 into a toilet. The rigid or semi-rigid nature of the tube 152 will prevent buckling and support the bag 150 so it will retain its shape as the urine collected in the bag 150 is drained. After the urine has been drained from the urine collection bag 150, the entire assembly can be appropriately discarded which will then complete the self-intermittent catheterization procedure.

While described in connection with the embodiment of FIG. 9, it will be appreciated that the same manner of use applies to FIG. 9a with the only exception being that the tube 152' is generally U-shaped and, thus, urine drained from the bladder will exit the tube 152' and enter the bag 150 near the corner of the bag 150 defined by the short edge 162a and the long edge 159b.

With regard to use of the intermittent catheter assembly 20 illustrated in FIGS. 1-4, the user can place a finger or thumb or finger through the finger loop 40 and separate a portion of the shrink wrap foil cover 42 using the tear slit 44 to form a handle 42a as shown in FIG. 3. Next, the user can use the other hand to grip the package or tray 27 behind the introducer tip 38 as at 27a in FIG. 3 to insert the cone-shape end 38a of the introducer tip 38 into the urethral opening until the flange 38b abuts the urethral opening. Next, the user can use the thumb or finger placed through the finger loop 40 to pull on the drawstring 26. This will cause the proximal insertion end 22a of the intermittent catheter 22 to be drawn through the opening 30 into the urethral opening. Further pulling on the drawstring 26 will cause the proximal insertion end 22a to be drawn through the urethra and into the bladder. The user will stop pulling on the drawstring 26 when urine starts to flow. This will be visually evident as urine from the bladder passes through the intermittent catheter, into the package or tray 27, and through the funnel 50. At this point, the proximal insertion end 22a will be properly located in the bladder and at least part of the insertable portion 22c will be located within the urethra with the distal end still within the package or tray 27.

Unlike the embodiment of FIGS. 9 and 9a, the intermittent catheter assembly 20 does not comprise a urine collection bag but, rather, is configured to permit urine being drained from the bladder to flow through it. However, the funnel 50 can either be attached to a urine collection bag, or it can be attached to a tube leading to a urine collection bag or for directing urine into a toilet, or the funnel can be used to direct urine into the toilet. Since urine being drained by the intermittent catheter 22 can flow through the channel 25 to the urine drainage opening 48, the funnel 50 can be used in any conventional way for disposing of the urine from the bladder.

While the foregoing sets forth details of the disclosure, it will be appreciated by those skilled in the art that the details herein given may be varied without departing from the true spirit and scope of the appended claims.

What is claimed is:

1. A packaged intermittent catheter assembly, comprising:
a package defining a cavity, an opening in the package and an intermittent catheter within the cavity, the intermittent catheter having a proximal insertion end at or near the opening, a distal end remote from the proximal insertion end, and an insertable portion extending from the proximal insertion end to a point approaching the distal end;
a generally U-shaped guide channel extending from the opening in the package through at least a portion of the cavity wherein the intermittent catheter is disposed within and guided by the guide channel during withdrawal from the cavity through the opening in the package;
wherein the guide channel remains within the package during withdrawal; and
a drawstring having a first portion disposed within the package and secured to the intermittent catheter and a second portion extending from the package at or near the opening in the package, wherein withdrawal of the drawstring from the package withdraws the intermittent catheter from the cavity through the opening in the package and into and through the urethra.

2. The assembly of claim 1 including a lubricating mechanism located within the package for lubricating at least the proximal insertion end of the intermittent catheter prior to withdrawal of the intermittent catheter from the cavity through the opening in the package, the lubricating mechanism comprising a gel lubricant for contact with at least the proximal insertion end of the intermittent catheter prior to or during withdrawal of the proximal insertion end of the intermittent catheter through the opening in the package.

3. The assembly of claim 1 further including a hydrophilic surface on at least the proximal insertion end and the insertable portion of the intermittent catheter.

4. The assembly of claim 1 wherein the package includes an introducer tip disposed on the package externally of the cavity and defining the opening through which the proximal insertion end and the insertable portion of the intermittent catheter is withdrawn.

5. The assembly of claim 1 wherein the drawstring includes a first end secured to the intermittent catheter and a second end outside of the package and including a finger loop associated with the second end of the drawstring for withdrawing the intermittent catheter.

6. The assembly of claim 1 wherein the drawstring has an end secured to the catheter between the insertable portion and the distal end portion of the catheter.

7. The assembly of claim 1 wherein the package comprises a tray.

8. The assembly of claim 1 wherein the package comprises a urine collection bag.

9. A packaged intermittent catheter assembly, comprising:
a urine collection bag formed to have a generally U-shaped guide channel therein and an opening therethrough, an intermittent catheter in the guide channel having a proximal insertion end and a distal end remote therefrom, the intermittent catheter also having an insertable portion extending from the proximal insertion end to a point approaching the distal end thereof, the proximal insertion end of the intermittent catheter being disposed at or near the opening in the bag; and
a drawstring having a first portion disposed within the urine collection bag and secured to the intermittent catheter and a second portion extending from the bag at or near the opening in the bag, and wherein withdrawal of the drawstring from the urine collection bag withdraws the intermittent catheter from the guide channel through the opening in the urine collection bag and into and through the urethra;
wherein the guide channel remains within the urine collection bag during withdrawal.

10. The assembly of claim 9 wherein the generally U-shaped guide channel extends from the opening in the bag to a point remote therefrom and wherein the intermittent catheter is disposed within and guided by the channel during withdrawal through the opening in the bag.

11. The assembly of claim 9 wherein the bag is generally rectangular and the guide channel is formed of a U-shaped tube having leg portions adjacent and generally parallel to each of a pair of opposed long edges of the bag and a gripping handle comprising a sealed void in the bag.

12. The assembly of claim 11 wherein the gripping handle is disposed between the leg portions of the U-shaped tube closer to one of the leg portions than the other of the leg portions and adjacent one of a pair of short edges of the bag and including a sealed drainage port.

13. The assembly of claim 12 wherein the drainage port is adjacent one of the long edges of the bag corresponding to the other of the leg portions of the U-shaped tube and adjacent the one of the pair of short edges of the bag and the drainage port is sealed by a peelable seal.

14. The assembly of claim 13 wherein the peelable seal has a finger hole accessible through a cut-out defined by the sealed void comprising the gripping handle for removing the peelable seal while gripping the tube through the gripping handle to drain the bag through the drainage port.

15. The assembly of claim 9 including a lubricating mechanism located within the bag for lubricating at least the proximal insertion end of the intermittent catheter prior to or during withdrawal of the intermittent catheter from the channel through the opening in the bag, the lubricating mechanism comprises a gel lubricant for contact with at least the proximal insertion end of the intermittent catheter prior to or during withdrawal of the proximal insertion end of the intermittent catheter from the bag.

16. The assembly of claim 9 further including a hydrophilic surface on at least the proximal insertion end and the insertable portion of the intermittent catheter.

* * * * *